(12) United States Patent
Nord et al.

(10) Patent No.: US 12,186,588 B2
(45) Date of Patent: *Jan. 7, 2025

(54) KNOWLEDGE BASED MULTI-CRITERIA OPTIMIZATION FOR RADIOTHERAPY TREATMENT PLANNING

(71) Applicant: Varian Medical Systems International AG, Cham (CH)

(72) Inventors: Janne Nord, Espoo (FI); Esa Kuusela, Espoo (FI); Joakim Pyyry, Helsinki (FI); Jarkko Peltola, Tuusula (FI); Martin Sabel, Hagendorn (CH)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/102,642

(22) Filed: Jan. 27, 2023

(65) Prior Publication Data

US 2023/0173303 A1   Jun. 8, 2023

Related U.S. Application Data

(63) Continuation of application No. 14/852,024, filed on Sep. 11, 2015, now Pat. No. 11,565,126.

(51) Int. Cl.
   *A61N 5/10*   (2006.01)
   *G16H 20/40*  (2018.01)

(52) U.S. Cl.
   CPC ......... *A61N 5/1031* (2013.01); *A61N 5/1038* (2013.01); *G16H 20/40* (2018.01);
   (Continued)

(58) Field of Classification Search
   CPC ................ A61N 5/1031; A61N 5/1038; A61N 2005/1041; A61N 2005/1074; G16H 20/40
   See application file for complete search history.

(56) References Cited

U.S. PATENT DOCUMENTS

| | | | |
|---|---|---|---|
| 11,565,126 B2 | 1/2023 | Nord et al. | |
| 2003/0233123 A1* | 12/2003 | Kindlein | A61N 5/1001 607/2 |

(Continued)

FOREIGN PATENT DOCUMENTS

| | | | | |
|---|---|---|---|---|
| EP | 2899659 A1 * | 7/2015 | ........... | A61N 5/1031 |
| WO | 2014205128 A1 | 12/2014 | | |

OTHER PUBLICATIONS

Kaliszewski et al., Evolutionary Multiobjective Optimization for Intensity Modulated Radiation Therapy, 2015, Multiple Criteria Decision Making, vol. 10, pp. 82-92. (Year: 2015).*

(Continued)

*Primary Examiner* — Christopher L Gilligan
(74) *Attorney, Agent, or Firm* — Harness, Dickey & Pierce, P.L.C.

(57) ABSTRACT

A method of generating a treatment plan for treating a patient with radiotherapy, the method includes obtaining a plurality of sample plans, which are generated by use of a knowledge base comprising historical treatment plans and patient data. The method also includes performing a multi-criteria optimization based on the plurality of sample plans to construct a Pareto frontier, where the plurality of sample plans are evaluated with at least two objectives measuring qualities of the plurality of sample plans such that treatment plans on the constructed Pareto frontier are Pareto optimal with respect to the objectives. The method further includes identifying a treatment plan by use of the constructed Pareto frontier.

20 Claims, 4 Drawing Sheets

(52) U.S. Cl.
CPC ............... *A61N 2005/1041* (2013.01); *A61N 2005/1074* (2013.01)

(56) References Cited

U.S. PATENT DOCUMENTS

| | | | |
|---|---|---|---|
| 2009/0037150 A1* | 2/2009 | Craft | G16H 50/50 |
| | | | 703/1 |
| 2011/0006215 A1 | 1/2011 | Van Heteren et al. | |
| 2011/0301977 A1* | 12/2011 | Belcher | G16H 40/63 |
| | | | 715/764 |
| 2012/0014507 A1* | 1/2012 | Wu | A61N 5/1031 |
| | | | 378/65 |
| 2012/0136194 A1* | 5/2012 | Zhang | A61N 5/103 |
| | | | 600/1 |
| 2013/0197878 A1* | 8/2013 | Fiege | G06F 30/20 |
| | | | 703/2 |
| 2014/0350322 A1 | 11/2014 | Schulte et al. | |
| 2015/0202464 A1 | 7/2015 | Brand et al. | |
| 2016/0129282 A1* | 5/2016 | Yin | G16H 40/20 |
| | | | 600/1 |
| 2018/0043182 A1 | 2/2018 | Wu et al. | |

OTHER PUBLICATIONS

Wang et al., Patient feature based dosimetric Pareto front prediction in esophageal cancer radiotherapy, Feb. 2015, Medical Physics, vol. 42, Iss. 2, pp. 1005-1011. (Year: 2015).*

Craft et al., "Deliverable navigation for multicriteria step and shoot IMRT treatment planning", Dec. 6, 2012, Institute of Physics and Engineering in Medicine, Physics in Medicine and Biology, pp. 87-102. (Year: 2012).

Ghandour et al., "Volumetric-modulated arc therapy planning using multicriteria optimization for localized prostate cancer", Jan. 23, 2015, Journal of Applied Clinical Medical Physics, vol. 16, No. 3, pp. 258-269. (Year: 2015).

Marleen Balvert, et al: "A Framework for Inverse Planning of Beam-on Times for 3D Small Animal Radiotherapy Using Interactive Multi-Objective Optimisation", Physics in Medicine and Biology, Institute of Physics Publishing, Bristol, GB, vol. 60, No. 14, Jul. 6, 2015, pp. 5681-5684.

Wang Jiazhou, et al.: "Patient Feature Based Dosimetric Pareto Front Prediction in Esophageal Cancer Radiotherapy", Medical Physics, AIP, Melville, NY, US. vol. 42, No. 2, Jan. 29, 2015, pp. 1005-1011.

Zarepisheh Masaoud et al,: "A Multicriteria Framework With Voxel-Dependent Parameters for Radiotherapy Treatment Plan Optimization", Medical Physics, AIP, Melville, NY, US, vol. 41, No. 4, Mar. 19, 2014, pp. 041705-1 to 041705-10.

Masoud Zarepisheh et al,: "A DVH-Guided IMRT Optimization Algorithm for Automatic Treatment Planning and Adaptive Radiotherapy Replanning", Medical Physics, vol. 41, No. 6, Jun. 1, 2014, pp. 061711-1 to 061711-14.

Craft David et al., "An Approach for Practical Multiobjective IMRT Treatment Planning", International Journal of Radiation: Incology Biology Physics, vol. 69, No. 5, Aug. 1, 2007, pp. 1600-1607.

Thieke et al,: "A New Concept for Interactive Radiotherapy Planning with Multicriteria Optimization: First Clinical Evaluation", Radiotherapy and Oncology, Elsevier, Ireland, vol. 85, No. 2, Nov. 1, 2007. pp. 292-298.

* cited by examiner

KNOWLEDGE BASED MULTI-CRITERIA OPTIMIZATION FOR RADIOTHERAPY TREATMENT PLANNING

CROSS-REFERENCE TO RELATED APPLICATION

This is a continuation application of co-pending U.S. patent application Ser. No. 14/852,024 entitled "Knowledge Based Multi-Criteria Optimization For Radiotherapy Treatment Planning," by Janne NORD et al., filed Sep. 11, 2015, which is hereby incorporated by reference.

TECHNICAL FIELD

This description relates generally to the field of radiotherapy, and more particularly to radiotherapy treatment plan development.

BACKGROUND

Radiation therapy treatment plan development generally employs medical imaging, such as X-ray, computed tomography (CT), magnetic resonance imaging (MM), or the like. Typically, a series of two-dimensional patient images, each representing a two-dimensional cross-sectional "slice" of the patient anatomy, are used to reconstruct a three-dimensional representation of a volume of interest (VOI), or structure of interest, from the patient anatomy.

The VOI typically includes one or more organs of interest, often including a planning target volume (PTV), such as a malignant growth or an organ including malignant tissue targeted for radiation therapy; a relatively healthy organ at risk (OAR) in the vicinity of a malignant growth at risk of radiation therapy exposure; or a larger portion of the patient anatomy that includes a combination of one or more PTVs along with one or more OARs. The objective of the radiation therapy treatment plan development typically aims to irradiate as much of the PTV as near the prescription dose as possible, while attempting to minimize irradiation of nearby OARs.

The resulting radiation therapy treatment plans are used during medical procedures to selectively expose precise areas of the body, such as malignant tumors, to specific doses of radiation in order to destroy the undesirable tissues. During the development of a patient-specific radiation therapy treatment plan, information generally is extracted from the three-dimensional model to determine parameters such as the shape, volume, location, and orientation of one or more PTVs along with one or more OARs.

Some radiotherapy planning tools take into account additional factors having a significant impact on the effectiveness of the radiation dose by consulting with a knowledge base which records patient geometric data together with previously administered treatment plans. The knowledge base further analyzes the relations between patient geometries and a variety of plan quality metrics, e.g., dose volume histogram (DVH), distance to target histogram (DTH), etc. An estimation model targeting specific treatment regions can be trained by the above described analysis, and a treatment plan can be predicted for a new patient with differing geometry by use of the estimation model.

Some other radiotherapy planning tools utilize a multiple criteria optimization (MCO) based approach to explore a multitude of treatment plans pertaining to a range of trade-offs between the PTV coverage and different OAR sparing options corresponding to a variety of plan quality metrics. However, even an approximated MCO approach, populated with a lesser number of initial treatment plans, still requires a large amount of computation in order to construct a Pareto frontier, not to mention that oftentimes, the sample treatment plans are randomly selected without sufficient clinical relevance with regard to the VOIs of a particular treatment plan.

SUMMARY

According to one embodiment of the present invention, a method of generating a treatment plan for treating a patient with radiotherapy includes obtaining a number of sample plans, which are generated by use of a knowledge base comprising historical treatment plans and patient data. The method also includes performing a multi-criteria optimization based on the sample plans to construct a Pareto frontier, whereby the sample plans are evaluated with at least two objectives measuring qualities of the sample plans such that treatment plans on the constructed Pareto frontier are Pareto optimal with respect to the objectives. The method further includes identifying a treatment plan for use by the constructed Pareto frontier.

According to another embodiment of the present invention, a system for generating a treatment plan for treating a patient with radiotherapy is provided. The system includes a memory that stores machine-readable instructions and a processor operable to execute the instructions to obtain a plurality of sample plans, which are generated by use of a knowledge base comprising historical treatment plans and patient data. The processor also performs a multi-criteria optimization based on the plurality of sample plans to construct a Pareto frontier, whereby the plurality of sample plans are evaluated with at least two objectives. These two objectives pertain to measuring qualities of the plurality of sample plans such that the treatment plans on the constructed Pareto frontier are Pareto optimal with respect to the objectives. The processor further identifies a treatment plan for use by the constructed Pareto frontier.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
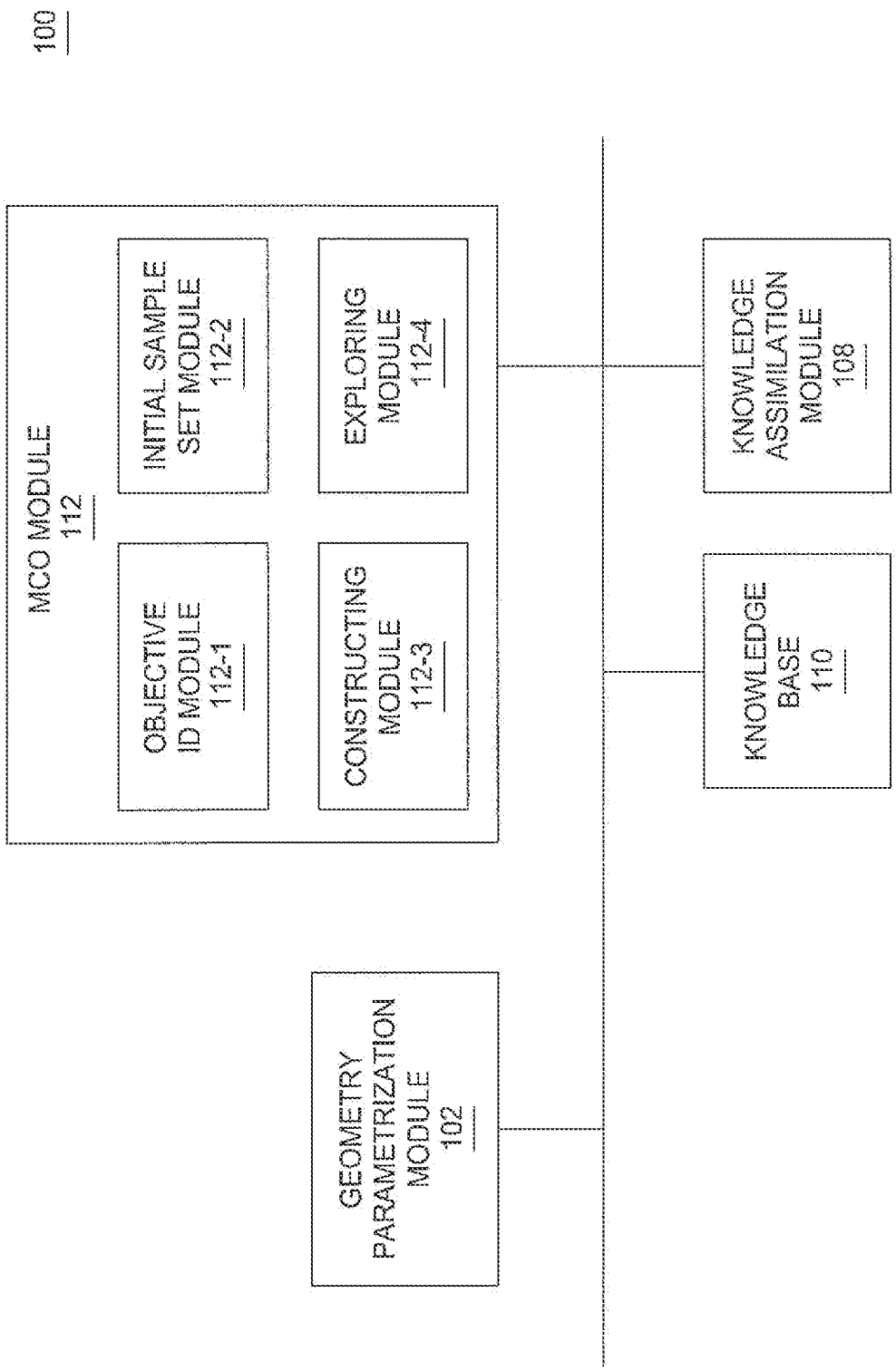
FIG. 1 is a schematic view illustrating an exemplary treatment planning tool that employs knowledge based MCO to generate radiotherapy treatment plans in accordance with an embodiment of the present invention.

An embodiment of the present invention is shown in FIG. 1, which illustrates an exemplary treatment planning tool 100 that utilizes knowledge based MCO to generate optimized patient-specific radiotherapy treatment plans. The treatment planning tool 100 includes a patient geometry parametrization module 102, a knowledge assimilation module 108, a knowledge base 110 and a MCO module 112. The treatment planning tool 100 correlates dose distributions achieved in or derived from actual patients in prior radiotherapy treatments with an initial population of treatment plans to construct a Pareto optimal set of treatment plans. With a constructed Pareto optimal set of treatment plan, a clinician can explore the possibilities in the PTV coverage and/or various OAR sparing options to identify an optimized treatment plan customized for a particular patient's anatomy or geometry.

Pareto optimality refers herein to the concept that a solution is a Pareto improvement if a change to a different solution makes at least one objective better off without making any other objectives worse off. A Pareto improvement is Pareto optimal or Pareto efficient if no further Pareto improvement can be made. With a Pareto frontier, by restricting attention to a set of objectives that are Pareto optimal, the clinician can make trade-offs within such a set, rather than considering the full range of every parameter.

A Pareto frontier is a set of solutions in an N-dimensional objective space that are Pareto optimal in light of a defined method of evaluation of those solutions. For the purposes of forming treatment plans, an N-dimensional Pareto frontier comprises a collection of treatment plans which accommodate the objectives of treatment.

The patient geometry parametrization module 102 generates a set of parameters, or metrics, based on the individual patient anatomic geometry with respect to various factors that affect dose distribution. It is known in the art that the dose level outside of a target structure decreases with linear, or Euclidean, distance from the target structure. However, additional geometric features can affect dose distribution. Metrics that take into account additional geometric features offer relatively improved correlation between predicted dose distribution and structure positions in the patient geometry.

Examples of dose metrics in addition to OAR-target proximity include, but are not limited to, the volume of the target structure, the volume of an organ at risk (OAR), any portion of the OAR that is not located within the field of the radiation beam, the number and orientation of applied fields, field geometry, target and OAR tissue densities, the prescription dose, and the like. For example, various metrics can take into account the number of fields that converge at each point in the patient geometry, or any organ passed through by a field before reaching the target volume. Additional metrics can account for tissue characteristics; for example, the Hounsfield unit (HU) scale can represent energy deposition and dispersion characteristics.

The knowledge assimilation module 108 extracts major dosimetric features from existing datasets representing the actual historical patient population. Those datasets provide for training datasets and validation datasets for the purposes of generating prediction models by retrospectively analyzing factors affecting the qualities of the clinical treatment plans. In such knowledge-based dose prediction, information gleaned from actual historical plans is used to estimate the achievable dose distribution regarding a new patient. For example, patient geometry and dose information of multiple historical treatment plans is mapped into a prediction model that can be used for dose prediction without storing all of the information from the original set of plans.

The knowledge base 110 stores the existing datasets representing a historical population of actual patient anatomical, treatment plans together with the achieved dose information, as well as prediction models trained by the datasets therein. In some embodiments, the systems described herein are further updated with optimal treatment plans identified by use of the MCO approach such that the systems can self learn, maintain and provide updated training sets, validation sets, as well as updated prediction models.

The MCO module 112 performs multiple criteria optimization process on a plurality of sample plans in order to construct a Pareto frontier which accommodates multiple objectives of a treatment plan. The constructed Pareto frontier facilitates the generation of an optimal treatment plan to treat a new patient with radiation therapy. The MCO module 112 includes an objective identifying module 112-1, an initial population module 112-2, a constructor module 112-3 and a Pareto frontier exploring module 112-4.

The objective identifying module 112-1 is configured to identify the objectives for a treatment plan. In some embodiments, the objectives are competing objectives in the sense that an instance of improving one objective degrades another objective. In general, as radiation therapy delivers treatment dose for a PTV, the proximity of critical normal structures and surrounding normal tissue makes radiation therapy inherently risky for damaging the nearby healthy structures and tissues (OARs). Hence, one main objective of radiation therapy is to maximize the radiation dose or treatment effects for a PTV; while another main objective of radiation therapy is to minimize the radiation dose to the nearby one or more OARs. Furthermore, in planning an optimized treatment for a PTV with multiple OARs, the objective of minimizing the radiation dose to one OAR can nevertheless be a competing objective of minimizing the radiation dose to another OAR.

The initial population module 112-2 is configured to designate an initial set of sample treatment plan from which a Pareto frontier can be constructed utilizing a MCO algorithm. In some embodiments, the initial set of sample treatment plans are selected from the training datasets which are utilized the knowledge base assimilation module 108 to generate prediction models. In some other embodiments, the initial set of sample treatment plans are created from a prediction model trained by the training dataset of the knowledge base 110.

With the assistance of the knowledge base 110 and geometry parametrization module 102, the regions of most clinical interest and/or relevance are identified such as to obtain from the knowledge base 110 the most clinically relevant training dataset and/or the trained estimation models. Consequently, the initial population derived from either the training dataset or the estimation model forms a basis to construct a Pareto frontier of a higher degree of clinical relevance.

Each of the sample plan in the initial population set are evaluated with plan quality metrics including but not limited to: Equivalent Uniform Dose (EUD) for both a PTV and an OAR, dose volume indices, Tumor Control Probability (TCP), Normal Tissue Complication Probability (NTCP), Heterogeneity Index (HI), etc. The objectives identified for the MCO module 112 can be selected as a subset of the plan quality metrics predicted in the model of the knowledge base 110.

The constructing module 112-3 is configured to sample the initial population plan and to construct a Pareto frontier according to the objectives identified by the objective identifying module 112-1. Along the constructed Pareto frontier, a set of Pareto optimal plans are represented as providing the best possible coverage of the PTV and sparing of the OARs. In other words, the treatment plans identified in the Pareto optimal set are the optimal plans that accommodate the overall objectives intended by the clinician for the treatment.

A variety of standard algorithms known in the art can be utilized to construct a Pareto frontier. For example, a constraint based approach can be implemented to formulate a Pareto frontier. In some embodiments, the range of a plan quality metric can be adopted as a constraint on the metric either from the training dataset that is designated as the initial population or from the prediction model trained by the knowledge base. In the case of training dataset, the finite number of data in the training set presents an inherent range of metrics associated with the data. In the case where the initial population is designated by use of a prediction model, a range of metrics can also be obtained by generating a plurality of initial sample plans using the prediction model and obtaining the range of metrics of the plans presented in the initial population.

With the constraints on a plan quality metric identified, a Pareto frontier is capable of being constructed by varying the plan quality metrics within the identified constraints. For example, the varying can be conducted with evenly distributed metric intervals. For another example, the varying is conducted with a higher degree of density of sampling in a certain sub-range within the constraints. The variation of the Pareto sampling can correspond to any type of statistical parameters associated with the initial population. For example, a confidence level associated with a predicted sample plan by use of the prediction model can be a parameter for variation. For another example, the extreme values associated with the metrics corresponding to the data included in the training dataset can also be a parameter for creating Pareto samples.

In some embodiments, given a particular patient geometry, a DVH predicting model trained by the knowledge base 110 can be utilized to generate the ranges of DVHs for different OARs identified for the PTV in addition to the PTV. The mean dose for each OAR is designated as the starting plan quality metrics based on which the above described variations can be conducted. The most probable prediction of the dose is designated as the constraints on the dose distribution. Next, the mean dose is varied at an interval of one standard deviation to generate the Pareto samples. In the case where there are multiple OARs, one set of optimized plans (Pareto frontier) is to be generated with one OAR at a time.

The exploring module 112-4 is configured to enable a clinician to explore the generated set of optimal plans along the constructed Pareto frontier such that the clinician can make a selection amongst conflicting objectives subject to a set of selected preference and configure multi-objective treatment plans to meet the objectives in an optimized manner.

Various implementations can be adopted to explore the trade-off possibility by assistance of the constructed Pareto frontier. In some embodiments, a minimum Euclidean distance criterion is utilized such that a point on the Pareto frontier closest to the point corresponding to the selected trade off is the identified treatment plan. In some other embodiments, a continuous Pareto boundary can be formed by interpolating through the individual Pareto optimal plans on the Pareto frontier such that a target point corresponding to intended trade-offs is mapped onto the Pareto boundary.

In some other alternative embodiments, the clinician can explore the constructed Pareto frontier by communicating trade-offs in the plan quality metric space to the treatment planning tool 100. Those trade-offs are communicated to the clinician by the planning tool 100 such that the clinician is aware of the scope and availability of those trade-offs that can be interactively tuned with the planning tool 100. Given a specific combination of one or more clinician selected trade-offs, a weighted combination of plans that satisfies all the selected metrics with specified trade-offs will be presented to the clinician. In some embodiments, linear programming or other suitable algorithms known in the art can be utilized to generate a combination plan weighted with the specified trade-offs. Furthermore, in some other embodiments, a machine control point sequence that can be delivered by a treatment machine is produced from the combination plan. For example, fluences associated with the sample treatment plans are combined to produce fluences for the combined treatment plan. The combined fluences is then converted to a machine deliverable control point sequence by a leaf sequencing algorithm or the like.

Figure 2:
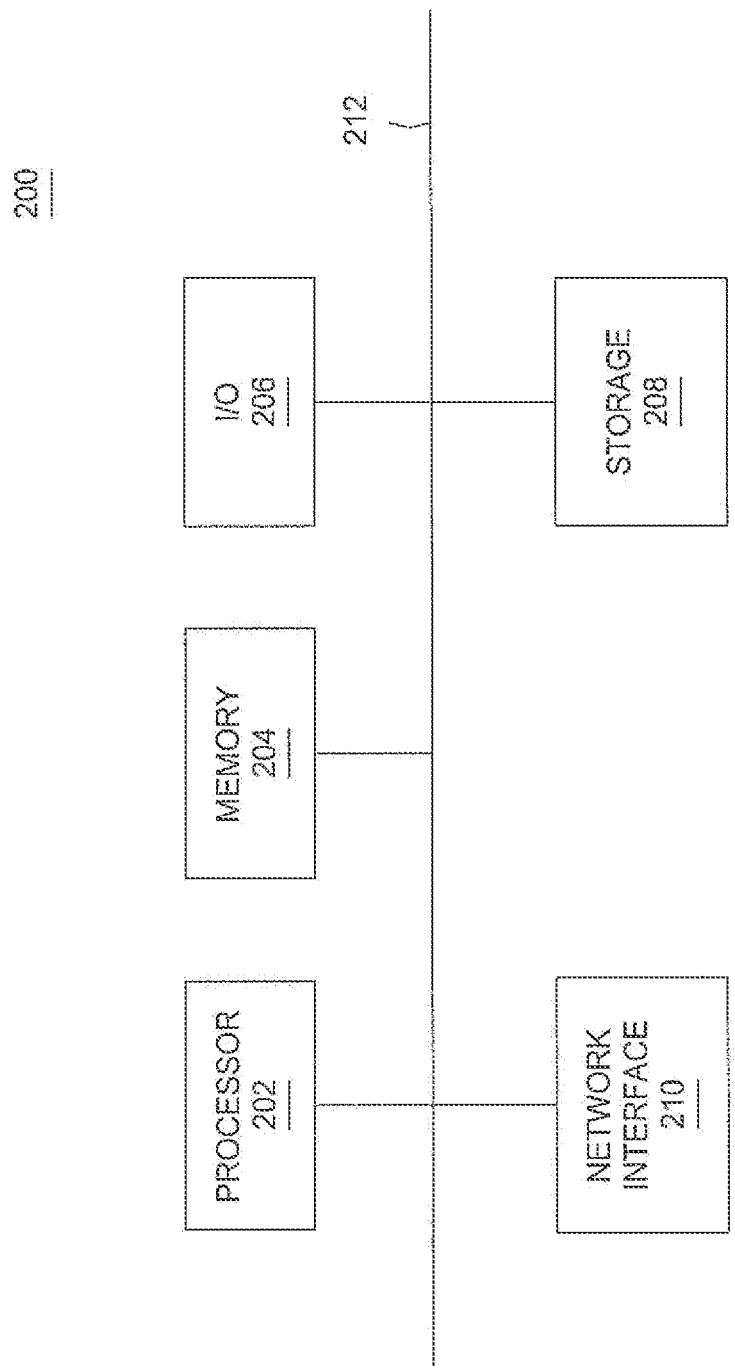
FIG. 2 is a schematic view illustrating an exemplary general computing system that can implement the dose distribution planning tool of FIG. 1.

As illustrated in FIG. 2, an exemplary general computing device 200 that can be employed in the treatment planning tool 100 of FIG. 1 includes a processor 202, a memory 204, an input/output device (I/O) 206, storage 208 and a network interface 210. The various components of the computing device 200 are coupled by a local data link 212, which in various embodiments incorporates, for example, an address bus, a data bus, a serial bus, a parallel bus, or any combination of these.

The computing device 200 communicates information to and requests input from the user or other devices by way of the I/O 206, which in various embodiments incorporates, for example, an interactive, menu-driven, visual display-based user interface, or graphical user interface (GUI), a pointing device, a voice activated device, a gesture activated device such that the user may interactively input information using direct manipulation and navigation of the user interface.

The computing device 200 can be coupled to a communication network by way of the network interface 210, which in various embodiments incorporates, for example, any combination of devices—as well as any associated software or firmware—configured to couple processor-based systems, including modems, access points, network interface cards, LAN or WAN interfaces, wireless or optical interfaces and the like, along with any associated transmission protocols, as may be desired or required by the design.

The computing device 200 can be used, for example, to implement the functions of the components of the treatment planning tool 100 of FIG. 1. In various embodiments, the computing device 200 can include, for example, a server, a controller, a workstation, a mainframe computer, personal computer (PC), a note pad, a computing tablet, a personal digital assistant (PDA), a smart phone, a wearable device, or the like. Programming code, such as source code, object code or executable code, stored on a computer-readable medium, such as the storage 208 or a peripheral storage component coupled to the computing device 200, can be loaded into the memory 204 and executed by the processor 202 in order to perform the functions of the treatment planning tool 100.

Figure 3:
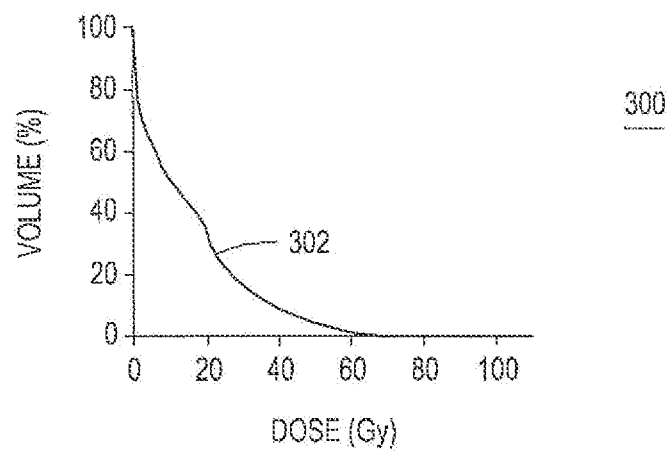
FIG. 3 is an illustration of an exemplary model predicting the DVHs for a VOI in accordance with an embodiment of the present disclosure.

FIG. 3 shows an exemplary DVH prediction model trained by a knowledge base in accordance with embodiments of the present disclosure. As a primary evaluation criterion for the treatment plan quality, a DVH graph 300 illustrates cumulative volume as a function of dose for a given VOL Here, a DVH predicted by the prediction model is depicted as the curve 302 for an OAR. DVH models can be trained to estimate DVHs for various VOIs, (i.e., one or more PTVs), as well as one or more OARs.

Figure 4A:
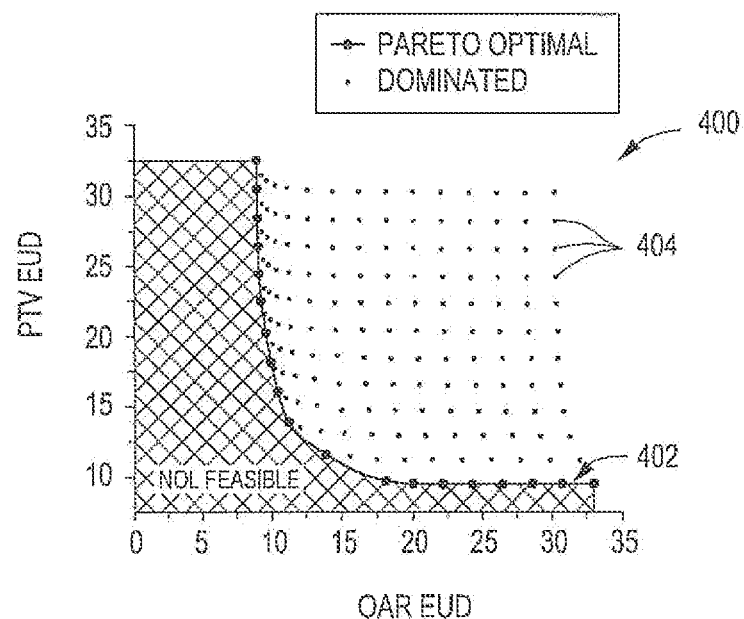
FIG. 4A is an illustration of an exemplary two dimensional Pareto frontier constructed for two exemplary objectives of Equivalent Uniform Dose (EUD) in a PTV and EUD in an OAR in accordance with an embodiment of the present disclosure.

FIG. 4A illustrates an exemplary two dimensional Pareto frontier constructed for two exemplary objectives of EUD in a PTV and EUD in an OAR in accordance with an embodiment of the present disclosure. The number of dimensions of a Pareto frontier can be constructed to an N-dimensional according to a number (N) of the objectives of treatment plans identified by the objective identification module 112-1. For the purposes of simplicity and illustration, a two-dimensional Pareto graph is described in below to optimize the competing objectives of achieving maximal EUD in a PTV and minimal EUD in one OAR. The dominated Pareto samples 404 are formed by the constructing module 112-3 of the MCO module 112 as described hereinabove. The Pareto frontier 402 is constructed by any algorithms known in the art to solve a multiple criteria optimization problem. As shown here in FIG. 4A, Pareto optimal points (representing treatment plans) A, B, C, etc. are a plurality of discrete points forming the set of Pareto optimal plans.

Figure 4B:
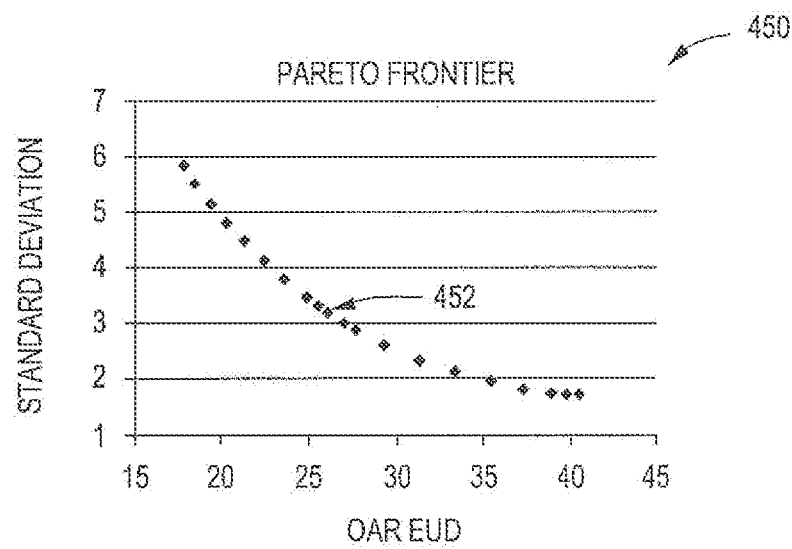
FIG. 4B is an illustration of another exemplary two dimensional Pareto frontier constructed for two exemplary objectives of standard deviation in a PTV and EUD in an OAR in accordance with an embodiment of the present disclosure.

FIG. 4B illustrates another exemplary two dimensional Pareto frontier constructed for two exemplary objectives of standard deviation in a PTV and EUD in an OAR in accordance with an embodiment of the present disclosure. Again, only two competing objectives are identified for the two dimensional Pareto frontier 452 for the purposes of simplicity and illustration. The objectives pertaining to the PTV related treatment quality are alternatively measured in standard deviations from a mean dose identified by use of the knowledge base of the treatment planning tool 100. The competing objective pertaining to the OAR is similarly measured in EUD as the Pareto frontier of FIG. 4A.

Figure 5:
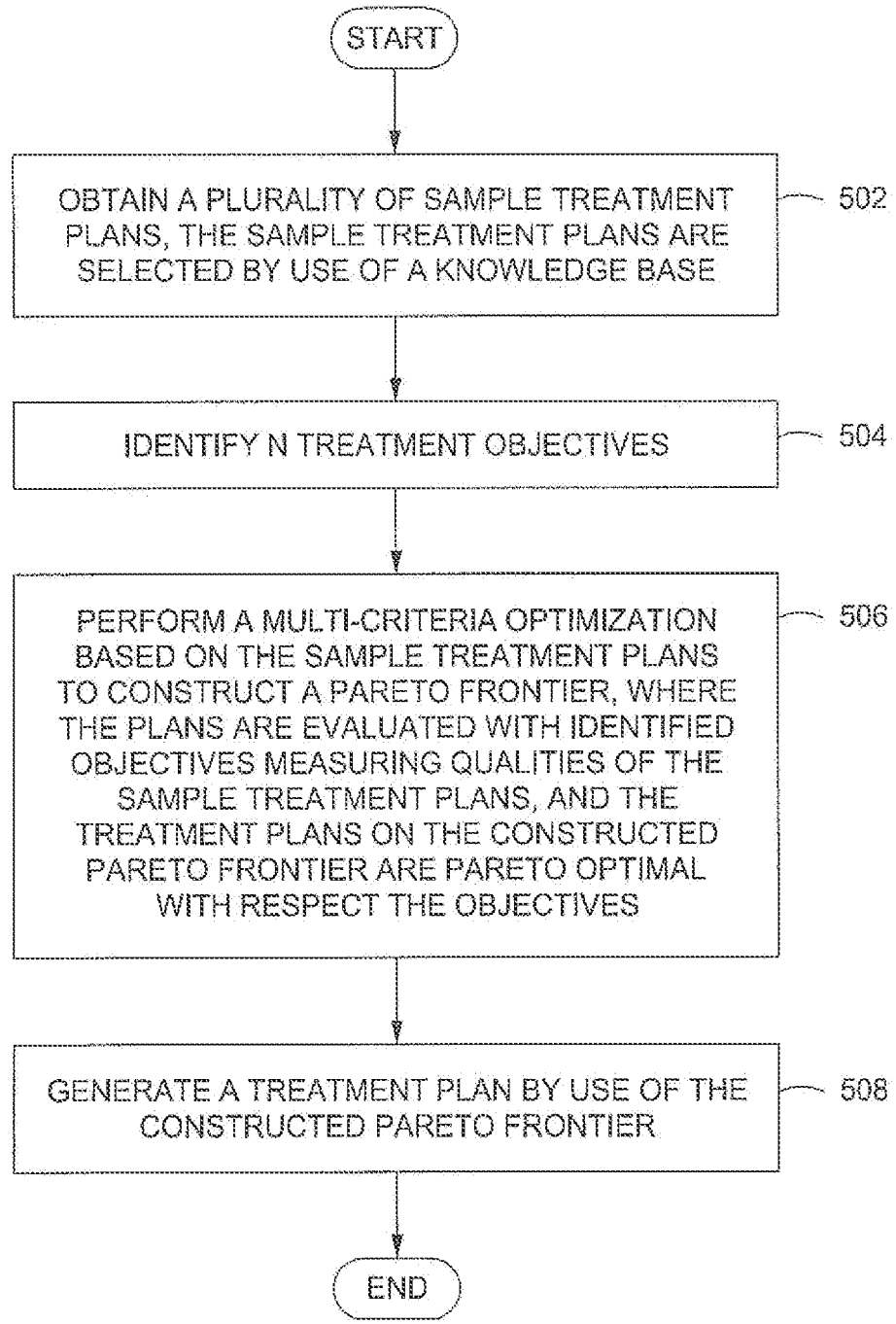
FIG. 5 is flow chart of an exemplary method of generating a treatment plan by use of a knowledge based MCO approach in accordance with an embodiment of the present disclosure.

FIG. 5 shows an exemplary method of generating a treatment plan by use of a knowledge based MCO approach in accordance with embodiments of the present disclosure. The generated treatment plan achieves optimized treatment objectives for a particular patient. The method 500 begins at step 502, whereby a number of sample treatment plans are obtained as a basis to construct a Pareto frontier. This initial population of sample plans can be selected from a knowledge base which records the historical patient geometry data together with administered treatment plans. For example, a sample plan of the initial population can be selected from the training dataset that bear the most clinical relevance to the particular patient treatment. For another example, a sample plan of the initial population is also be obtained by use of a prediction model trained by the knowledge base.

At step 504, a total number of N treatment objectives are identified for the optimization process. Such treatment objectives can also be selected with assistance from the training dataset or the prediction model utilized to generate the initial population. The plan metrics pertaining to the training set or estimated by the prediction model can be designated as the overall objectives for the treatment plan.

At step 506, a multiple criteria optimization is performed on the basis of the initial population and the identified objectives. Given N objectives, an N dimensional Pareto frontier is to be constructed accordingly by evaluating the plans with those objectives. Generic algorithms can be utilized to form the Pareto frontier which comprises a collection of treatment plans to accommodate the above identified objectives. In some embodiments, the clinician can designate one or more highest or lowest constraints for all objectives. The clinician has the ability to choose to minimize or maximize these constraints within those tolerances. For example, some treatment may choose to minimize the EUD in an OAR, while having the EUD for a PTV maintained at or below a certain level. Alternatively, such constraints can be obtained from the knowledge base by use of the training dataset and/or the prediction model as well.

In some embodiments, with the constraints on a plan quality metric identified, a Pareto frontier is constructed by varying the plan quality metrics within the identified constraints. For example, the varying is conducted with evenly distributed metric intervals. For another example, the varying can also be conducted with a higher degree of density of sampling in a certain sub-range within the constraints. The variation of the Pareto sampling corresponds to any type of statistical parameters associated with the initial population. For example, a confidence level associated with a predicted sample plan by use of the prediction model can be a parameter for variation. For another example, the extreme values associated with the metrics corresponding to the data included in the training dataset can also be a parameter for creating Pareto samples.

In some other embodiments, given a particular patient geometry, a DVH predicting model trained by the knowledge base is utilized to generate the ranges of DVHs for different OARs identified for the PTV. The mean dose for each OAR is designated as the starting plan quality metrics based on which the above described variations can be conducted. The most probable prediction of the dose are designated as the constraints on the dose distribution. Next, the mean dose is varied at an interval of one standard deviation to generate the Pareto samples. In the case where there are multiple OARs, one set of optimized plans (Pareto frontier) is to be generated for one OAR at a time.

At step 508, by use of a user interface that displays or presents the constructed Pareto frontier, the clinician navigates amongst the set of Pareto optimal treatment plans to identify one plan that best achieving the objectives of the treatment for a particular patient. If a plan corresponding to the particular treatment objectives is on the Pareto frontier, the Pareto optimal plan identifies an optimized treatment plan for the particular patient. Otherwise, the clinician explores the Pareto frontier such as to approximate a target point onto a point that is on the Pareto frontier.

A variety of methods can be employed to map a target point onto the Pareto frontier. In some embodiments, a minimum Euclidean distance criterion is utilized such that a point on the Pareto frontier closest to the point corresponding to the selected trade off is the identified optimal treatment plan. In some other embodiments, a continuous Pareto boundary is formed by interpolating through the individual Pareto optimal plans on the Pareto frontier such that a target point corresponding to intended trade-offs is mapped onto the Pareto boundary.

In some other alternative embodiments, the clinician can explore the constructed Pareto frontier by communicating trade-offs in the plan quality metric space to the treatment planning tool 100. Those trade-offs are communicated to the clinician by the planning tool 100 in the first place such that the clinician is aware of the scope and availability of those trade-off that is interactively tuned with the planning tool 100. Given a specific combination of one or more clinician selected trade-offs, a weighted combination of plans that satisfies all the selected metrics with specified trade-offs will be presented to the clinician. In some embodiments, linear programming or other suitable algorithm known in the art is utilized to generate a combination plan weighted with the specified trade-offs.

For example, with an N objective optimization space projected onto a two objective space, a slideable menu option can be provided to the clinician to distribute weights to the various objectives according to set of preferences with respect to a particular patient treatment. With clinician tuned objectives, the Pareto frontier accommodates different weights applied to the selected objectives of treatment to produce an optimized treatment plan.

Aspects of this disclosure are described herein with reference to flowchart illustrations or block diagrams, in which each block or any combination of blocks can be implemented by computer program instructions. The instructions may be provided to a processor of a general purpose computer, special purpose computer, or other programmable data processing system to effectuate a machine or article of manufacture, and when executed by the processor the instructions create means for implementing the functions, acts or events specified in each block or combination of blocks in the diagrams.

In this regard, each block in the flowchart or block diagrams may correspond to a module, segment, or portion of code that including one or more executable instructions for implementing the specified logical function(s). It should also be noted that, in some alternative implementations, the functionality associated with any block may occur out of the order noted in the figures. For example, two blocks shown in succession may, in fact, be executed substantially concurrently, or blocks may sometimes be executed in reverse order.

A person of ordinary skill in the art will appreciate that aspects of this disclosure may be embodied as a device, system, method or computer program product. Accordingly, aspects of this disclosure, generally referred to herein as circuits, modules, components or systems, may be embodied in hardware, in software (including firmware, resident software, micro-code, etc.), or in any combination of software and hardware, including computer program products embodied in a computer-readable medium having computer-readable program code embodied thereon.

In this respect, any combination of one or more computer readable media may be utilized, including, but not limited to, an electronic, magnetic, optical, electromagnetic, infrared, or semiconductor system, apparatus, or device, or any suitable combination of these. In the context of this disclosure, a computer readable storage medium may include any tangible medium that is capable of containing or storing program instructions for use by or in connection with a data processing system, apparatus, or device.

Computer program code for carrying out operations regarding aspects of this disclosure may be written in any combination of one or more programming languages. The program code may execute entirely on an individual personal computer, as a stand-alone software package, partly on a client computer and partly on a remote server computer, entirely on a remote server or computer, or on a cluster of distributed computer nodes.

It will be understood that various modifications may be made. For example, useful results still could be achieved if steps of the disclosed techniques were performed in a different order, and/or if components in the disclosed systems were combined in a different manner and/or replaced or supplemented by other components. Accordingly, other implementations are within the scope of the following claims.

What is claimed is:

1. A method of generating a treatment plan for treating a patient with radiotherapy, the method comprising:
   identifying a plurality of organs at risk for a planning target volume;
   obtaining a plurality of sample plans, wherein the plurality of sample plans are generated by use of a knowledge base comprising historical treatment plans and patient data;
   performing a multi-criteria optimization, based on the plurality of sample plans, to construct a Pareto frontier, wherein the plurality of sample plans are evaluated with at least two objectives measuring qualities of the plurality of sample plans, wherein the performing the multi-criteria optimization to construct the Pareto frontier comprises using a confidence level associated with a predicted sample plan, wherein treatment plans on the constructed Pareto frontier are Pareto optimal with respect to the objectives, wherein the performing the multi-criteria optimization further comprises generating a Pareto frontier with one organ at risk at a time of the plurality of organs at risk;
   receiving a selected tradeoff point on the constructed Pareto frontier;
   utilizing a minimum Euclidean distance criterion such that a point on the constructed Pareto frontier closest to the selected trade off point is an identified treatment plan; and
   generating the identified treatment plan by use of the constructed Pareto frontier, wherein said generating the identified treatment plan by use of the constructed Pareto frontier comprises generating (i) a combinational treatment plan comprising a combination of sample plans and (ii) a machine deliverable control point sequence corresponding to the combinational treatment plan, wherein the control point sequence is a sequence that can be delivered by a treatment machine.

2. The method of claim 1, wherein a sample plan of the plurality of sample plans is selected from training plans of the knowledge base.

3. The method of claim 1, wherein a sample plan of the plurality of sample plans is generated utilizing an estimation model of the knowledge base, wherein the estimation model is constructed by use of training plans of the knowledge base.

4. The method of claim 1, wherein the performing the multi-criteria optimization further comprises each of the plurality of sample plans is evaluated with a value related to a Tumor Control Probability (TCP).

5. The method of claim 1, wherein said generating the identified treatment plan by use of the constructed Pareto frontier is performed by adjusting plan metrics of the plurality of sample plans.

6. The method of claim 1, wherein the objectives are selected from plan quality metrics of the plurality of sample plans.

7. The method of claim 1, further comprising updating the knowledge base with the generated identified treatment plan.

8. The method of claim 1, wherein generating the machine deliverable control point sequence corresponding to the combinational treatment plan comprises:
   combining a plurality of fluences associated with the plurality of sample plans to form combined fluences; and transforming the combined fluences into a machine deliverable control point sequence using a leaf sequencing algorithm.

9. A system for generating a treatment plan for treating a patient with radiotherapy, the system comprising:
a memory that stores machine-readable instructions; and
a processor communicatively coupled to the memory, the processor operable to execute the instructions to
identify a plurality of organs at risk for a planning target volume;
obtain a plurality of sample plans, wherein the plurality of sample plans are generated by use of a knowledge base, the knowledge base comprising historical treatment plans and patient data;
perform a multi-criteria optimization, based on the plurality of sample plans, to construct a Pareto frontier, wherein the plurality of sample plans are evaluated with at least two objectives measuring qualities of the plurality of sample plans, wherein the perform the multi-criteria optimization to construct the Pareto frontier comprises use of a confidence level associated with a predicted sample plan, wherein treatment plans on the constructed Pareto frontier are Pareto optimal with respect to the objectives, wherein the perform the multi-criteria optimization further comprises generate a Pareto frontier with one organ at risk at a time of the plurality of organs at risk;
receive a selected tradeoff point on the constructed Pareto frontier;
utilize a minimum Euclidean distance criterion such that a point on the constructed Pareto frontier closest to the selected trade off point is an identified treatment plan; and
generate the identified treatment plan by use of the constructed Pareto frontier, wherein said generate the identified treatment plan by use of the constructed Pareto frontier comprises generate (i) a combinational treatment plan comprising a combination of sample plans and (ii) a machine deliverable control point sequence corresponding to the combinational treatment plan, wherein the control point sequence is a sequence that can be delivered by a treatment machine.

10. The system of claim 9, further comprising a displaying device, wherein at least a portion of the constructed Pareto frontier is presented on the displaying device.

11. The system of claim 9, wherein a sample plan of the plurality of sample plans is selected from training plans of the knowledge base.

12. The system of claim 9, wherein a sample plan of the plurality of sample plans is generated utilizing an estimation model of the knowledge base, wherein the estimation model is constructed by use of training plans of the knowledge base.

13. The system of claim 9, wherein the perform the multi-criteria optimization further comprises each of the plurality of sample plans is evaluated with a value related to a Normal Tissue Complication Probability (NTCP).

14. The system of claim 9, wherein said generate the identified treatment plan by use of the constructed Pareto frontier is performed by adjusting plan metrics of the plurality of sample plans.

15. The system of claim 9, wherein the objectives are selected from plan quality metrics of the plurality of sample plans.

16. The system of claim 9, wherein the processor is further operable to update the knowledge base with the generated identified treatment plan.

17. The system of claim 9, wherein the generate the machine deliverable control point sequence corresponding to the combinational treatment plan comprises:
combine a plurality of fluences associated with the plurality of sample plans to form combined fluences; and
transform the combined fluences into a machine deliverable control point sequence using a leaf sequencing algorithm.

18. A non-transitory computer readable storage medium having embedded therein program instructions, when executed by one or more processors of a device, causes the device to execute a process for generating a treatment plan for treating a patient with radiotherapy, the process comprising:
identifying a plurality of organs at risk for a planning target volume;
obtaining a plurality of sample plans, wherein the plurality of sample plans are generated by use of a knowledge base, the knowledge base comprising historical treatment plans and patient data;
performing a multi-criteria optimization, based on the plurality of sample plans, to construct a Pareto frontier, wherein the plurality of sample plans are evaluated with at least two objectives measuring qualities of the plurality of sample plans, wherein the performing the multi-criteria optimization to construct the Pareto frontier comprises using a confidence level associated with a predicted sample plan, wherein treatment plans on the constructed Pareto frontier are Pareto optimal with respect to the objectives, wherein the performing the multi-criteria optimization further comprises generating a Pareto frontier with one organ at risk at a time of the plurality of organs at risk;
receiving a selected tradeoff point on the constructed Pareto frontier;
utilizing a minimum Euclidean distance criterion such that a point on the constructed Pareto frontier closest to the selected trade off point is an identified treatment plan; and
generating the identified treatment plan by use of the constructed Pareto frontier, wherein said generating the identified treatment plan by use of the constructed Pareto frontier comprises generating (i) a combinational treatment plan comprising a combination of sample plans and (ii) a machine deliverable control point sequence corresponding to the combinational treatment plan, wherein the control point sequence is a sequence that can be delivered by a treatment machine.

19. The non-transitory computer readable storage medium of claim 18, wherein the performing the multi-criteria optimization further comprises each of the plurality of sample plans is evaluated with at least one of an Equivalent Uniform Dose (EUD) for a planning target volume (PTV), an EUD for an Organ at Risk (OAR), Dose Volume Indices (DVI), a Heterogeneity Index (HI), or a value related to a Normal Tissue Complication Probability (NTCP).

20. The non-transitory computer readable storage medium of claim 18, wherein generating the machine deliverable control point sequence corresponding to the combinational treatment plan comprises:
combining a plurality of fluences associated with the plurality of sample plans to form combined fluences; and transforming the combined fluences into a machine deliverable control point sequence using a leaf sequencing algorithm.

\* \* \* \* \*